(12) United States Patent
Weldon et al.

(10) Patent No.: US 7,591,199 B2
(45) Date of Patent: Sep. 22, 2009

(54) METHOD FOR MEASURING OF PARTICLES GENERATED FROM MEDICAL DEVICES OR INSTRUMENTS UTILIZED DURING SIMULATED CLINICAL APPLICATIONS

(75) Inventors: Lisa Weldon, Mountain View, CA (US); Greg Hyde, Menlo Park, CA (US); Ellen Roche, Galway (IE); Maithili Shrivastava, Irvine, CA (US)

(73) Assignee: Abbott Laboratories, Abbott Park, IL (US)

( * ) Notice: Subject to any disclaimer, the term of this patent is extended or adjusted under 35 U.S.C. 154(b) by 19 days.

(21) Appl. No.: 11/758,548

(22) Filed: Jun. 5, 2007

(65) Prior Publication Data
US 2008/0006081 A1 Jan. 10, 2008

Related U.S. Application Data

(60) Provisional application No. 60/811,277, filed on Jun. 6, 2006, provisional application No. 60/811,235, filed on Jun. 6, 2006.

(51) Int. Cl.
G01N 19/00 (2006.01)
(52) U.S. Cl. ..................................... 73/865.9
(58) Field of Classification Search ............... 73/865.6, 73/865.5, 865.9; 607/1
See application file for complete search history.

(56) References Cited

U.S. PATENT DOCUMENTS

| | | | |
|---|---|---|---|
| 2,704,897 A | 3/1955 | Lade | 434/272 |
| 4,384,578 A * | 5/1983 | Winkler | 604/114 |
| 6,517,354 B1 | 2/2003 | Levy | 434/262 |
| 2002/0116054 A1 | 8/2002 | Lundell et al. | 623/2.1 |
| 2004/0206158 A1 | 10/2004 | Edelman et al. | 73/37 |
| 2007/0185534 A1 * | 8/2007 | Conti et al. | 607/1 |
| 2008/0084959 A1 | 4/2008 | Weldon et al. | 377/10 |

FOREIGN PATENT DOCUMENTS

| | | |
|---|---|---|
| EP | 1365237 | 11/2003 |
| WO | WO2007/143688 | 6/2007 |

OTHER PUBLICATIONS

Office Action mailed Oct. 6, 2008, U.S. Appl. No. 11/758,544.

\* cited by examiner

*Primary Examiner*—Hezron Williams
*Assistant Examiner*—Tamiko D Bellamy

(57) ABSTRACT

An apparatus for measuring particles generated from a medical device includes a platform configured for retaining at least one medical device and at least one simulated body lumen tubing. The platform includes: a medical device receptacle dimensioned to retain a medical device; a pretest receptacle dimensioned to retain pretest tubing; and a test receptacle dimensioned to retain test tubing. The apparatus can be used for measuring particles generated from a medical device during a simulated clinical application by the following: introducing the medical device into the test tubing; causing fluid to flow through the pretest tubing, past the medical device, and through the test tubing; and counting the particles in the fluid downstream from the medical device.

19 Claims, 4 Drawing Sheets

METHOD FOR MEASURING OF PARTICLES GENERATED FROM MEDICAL DEVICES OR INSTRUMENTS UTILIZED DURING SIMULATED CLINICAL APPLICATIONS

CROSS-REFERENCE TO RELATED APPLICATIONS

The present U.S. patent application claims benefit of U.S. Provisional Application Ser. No. 60/811,277, filed Jun. 6, 2006, entitled "AN APPARATUS AND SYSTEM FOR MEASURING OF PARTICULATES GENERATED FROM MEDICAL DEVICES or INSTRUMENTS UTILIZED DURING SIMULATED CLINICAL APPLICATIONS" with Lisa Weldon, Greg Hyde, Ellen Roche, and Maithili Shrivastava as inventors, and of U.S. Provisional Application Ser. No. 60/811,235, filed Jun. 6, 2006, entitled "A METHOD FOR MEASURING OF PARTICULATES GENERATED FROM MEDICAL DEVICES or INSTRUMENTS UTILIZED DURING SIMULATED CLINICAL APPLICATIONS" with Lisa Weldon, Greg Hyde, Ellen Roche, and Maithili Shrivastava as inventors, which provisional applications are each incorporated herein by specific reference in their entirety.

BACKGROUND OF THE INVENTION

I. The Field of the Invention

The present invention relates to an apparatus, system, and method for measuring particles that are generated from medical devices or instruments that are delivered into or utilized within the body of a patient, such as a human patient. More particularly, the apparatus, system, and method can be used to perform real-time measurement of particles generated from medical devices or instruments in a manner and condition that closely or exactly mimics the manner and condition at which the medical devices or instruments would actually be utilized within the body of the patient. The apparatus, system, and methods are designed to study the release of particles from medical devices or instruments in a simulated clinical or surgical procedure that is closely related to the actual conditions in which the medical devices or instruments would be used.

II. The Related Technology

Stents, grafts, catheters, and a variety of other medical devices or instruments are well known to be used in various surgical and interventional procedures. The medical devices are usually delivered or utilized within the body of an animal, such as a human, for treating aneurysms, lining or repairing vessel walls, filtering or controlling fluid flow, expanding or scaffolding occluded or collapsed vessels, and for a variety of other surgical or interventional procedures. The medical devices, either alone or in combination with other medical devices, are often delivered into or used in virtually any accessible body lumen of an animal, and such medical devices can be deployed by any of a variety of recognized methodologies.

While the medical devices or instruments may be designed to be utilized within the body of an animal, such medical devices or instruments may inadvertently be susceptible to malfunctions that compromise the surgical or interventional procedures and compromise the health of the animal in which the medical device or instrument is employed. It has been established that medical devices and instruments that are prepared by industrial manufacturing methods for use within the body of an animal can crack, break, splinter, degrade, bend, flex, generate particles, and the like during use, all of which may result in particles being released from the medical device or instrument. When a medical device or instrument generates particles during deployment or use, such particles can cause additional complications and can compromise the health of the animal. For example, particle generation can cause organ damage, and increase the potential of stroke or heart attack. Thus, it can be desirable to determine whether or not a medical device or instrument generates particles during deployment or use, and it can further be desired to determine the amount of particles that are generated in these instances.

The current procedures for determining whether particles are generated from medical devices and measuring the amount of such generated particles are batch methods where the counting is done offline after the particles are generated. However, such procedures can be susceptible to error because the particles may fall out of solution or the sample may not contain an accurate representation of the entire population of particles. While all of the particles generated by a medical device could be counted in each procedure, this would be a monumental task that is not practical. Counting all particles in the visual method using a microscope would require an overly-burdensome amount of manual counting, time, and eye strain. The method using a current displacement-based particle counter (e.g., Coulter® counters) count discrete volumes making it very difficult to count all the particles without inducing air bubble errors. Laser counters that are used as batch counters have the same concerns as the current displacement-based particle counters. Thus, it is desirable for a procedure to count substantially all particles generated in real time rather than counting particles in a batch procedure, and there exists a need in the art for a way to measure the amount and size of particles generated from medical devices when utilized in mammals.

Therefore, it would be advantageous to have an apparatus, system, and method for determining whether a medical device generates particles or measuring the amount of such particles in a real-time or steady-state process. Additionally, it would be advantageous for the apparatus, system, and method to simulate the conditions imposed on a medical device when being delivered or utilized within the body of a patient. Further, it would be advantageous for the apparatus, system, and method to employ a stream of fluid that mimics or simulates blood flow so that any generated particles can be identified or measured in simulated blood flow.

BRIEF SUMMARY OF THE INVENTION

The present invention relates to an apparatus, system, and method for measuring particles that are generated from medical devices or instruments that are delivered into or utilized within the body of a patient, such as a human patient. More particularly, the apparatus, system, and method can be used to perform real-time measurement of particles generated from medical devices or instruments in a manner and condition that closely or exactly mimic the manner and condition at which the medical devices or instruments would actually be utilized within the body of the patient. The apparatus, system, and methods are designed to study the release of particles from medical devices or instruments in a simulated clinical or surgical procedure that is closely related to the actual conditions in which the medical devices or instruments would be used.

In one embodiment, the present invention includes an apparatus for measuring particles generated from a medical device during a simulated clinical application. Such an apparatus includes a platform configured for retaining at least one medical device and at least one simulated body lumen tubing. The platform includes the following: a medical device receptacle dimensioned to retain the at least one medical device; a pretest receptacle dimensioned to retain pretest tubing; and a test receptacle dimensioned to retain test tubing. The test receptacle has at least one substantially straight portion configured for straightening the test tubing when disposed therein, and at least one bent portion configured for bending the test tubing into a bent pathway when disposed therein. Additionally, the platform includes a junction that interconnects the medical device receptacle, pretest receptacle, and test receptacle.

In one embodiment, at least one of the medical device receptacle, pretest receptacle, or test receptacle includes a means for securing the medical device, pretest tubing, or test tubing to the platform. Accordingly, the means for securing can be selected from the group consisting of a fastener, lip, adhesive, top platform, housing, cover, contoured receptacle walls, or the like. Also, the medical device, pretest tubing, and test tubing can be disposed in their respective receptacles. Moreover, the pretest tubing can be fluidly coupled with the test tubing via a junction coupling disposed in the junction.

In one embodiment, a particle counter can be fluidly coupled to and downstream of the test tubing. Also, a pump can be fluidly coupled to a fluid pathway that is fluidly coupled to the pretest tubing and test tubing. Additionally, a temperature controller can be disposed at the fluid pathway that is fluidly coupled to the pretest tubing and test tubing, wherein the temperature controller is thermally coupled to the fluid pathway so as to control the temperature of a fluid flowing through the fluid pathway. Further, a flow meter can be disposed in the fluid pathway so as to measure the fluid flow rate of a fluid flowing through the fluid pathway. Furthermore, the apparatus can include a computing system in communication with at least one of the temperature controller, pump, flow meter, or particle counter, wherein the computing system is configured for receiving and/or transmitting data to the temperature controller, pump, flow meter, or particle counter.

In one embodiment, the present invention includes a system for measuring particles generated from a medical device during a simulated clinical application. Such a system can include a platform configured for retaining at least one medical device and at least one simulated body lumen tubing by including the following: a medical device receptacle dimensioned to retain the at least one medical device; a pretest receptacle dimensioned to retain pretest tubing; a test receptacle dimensioned to retain test tubing; and a junction that interconnects the medical device receptacle, pretest receptacle, and test receptacle. The system also includes a pump that can be disposed in a position relative to the platform, and that is fluidly coupled to a fluid pathway that is fluidly coupled to the pretest tubing and test tubing when disposed in the pretest receptacle and test receptacle, respectively, so as to be capable of pumping fluid through the pretest tubing and test tubing. Additionally, the system includes a particle counter that can be disposed in a position relative to the platform so as to be capable of being fluidly coupled to and/or downstream of the test tubing when disposed in the test receptacle. That is, the particle counter can be fluidly coupled to the fluid pathway or separate. Furthermore, the system can include the components described in connection with the apparatus as described herein.

In one embodiment, the system includes a fluid for use within the system. Such a fluid can simulate a body fluid, or can be a body fluid that includes blood, blood plasma, serum, cellular components, or the like. Additionally, the system can include control particles that may optionally be included within the fluid. Otherwise, the control particles can be dry or wet, and can be injected into the fluid within the fluid pathway by being injected through an injection port.

In one embodiment, the present invention includes an advanced system for measuring particles generated from a medical device during simulated clinical applications. Such a system includes a platform configured for retaining at least one medical device and at least one simulated body lumen tubing by having the following: a medical device receptacle dimensioned to retain at least one medical device; a pretest receptacle dimensioned to retain pretest tubing; a test receptacle dimensioned to retain test tubing, wherein the test receptacle has at least one substantially straight portion configured for straightening the simulated body lumen tubing when disposed therein, and at least one bent or tortuous portion configured for bending the simulated body lumen tubing into a bent or tortuous pathway when disposed therein; and a junction that interconnects the medical device receptacle, pretest receptacle, and test receptacle. The system also includes pretest tubing disposed in the pretest receptacle, test tubing disposed in the test receptacle, and junction coupling that couples the pretest tubing to the test tubing. Also, the system includes a fluid as described herein. Additionally, the system includes a pump disposed in a position relative to the platform, and fluidly coupled to a fluid pathway that is fluidly coupled to the pretest tubing and test tubing so as to be capable of pumping fluid through the pretest tubing and test tubing. Further, the system includes a particle counter disposed in a position relative to the platform so as to be capable of being fluidly coupled to and downstream of the test tubing. Furthermore, the system includes a temperature controller disposed relative to the platform at the fluid pathway so as to be thermally coupled to the fluid pathway, and capable of controlling the temperature of the fluid when flowing through the fluid pathway. Furthermore, the system includes a flow meter disposed in the fluid pathway so as to measure the fluid flow rate of a fluid flowing through the fluid pathway. A computing system is in communication with at least one of the temperature controller, pump, flow meter or particle counter so as to be capable of receiving and/or transmitting data to the temperature controller, pump, flow meter, or particle counter.

In one embodiment, the pump can include at least one of a gear pump, metering pump, syringe pump, roller-pump, centripetal pump, flow metering pump, or the like. Also, the temperature controller can include at least one of cardioplegic heat exchangers, heating devices associated with the platform, industrial heat exchangers, general heat exchangers, tube heat exchangers, batch heaters, water baths, inductive heaters, or the like. Additionally, the flow meter can include at least one of laser meters, rotometers, bubble meters, ultrasonic meters, electrical meters, magnetic meters, or the like. Further, the particle counter can include at least one of current displacing particle counters, laser counters, or the like.

In one embodiment, the medical device is disposed within the medical device receptacle, wherein the medical device is an endovascular device or instrument. As such, the medical device can be selected from the group consisting of stents, catheters, balloons, drug delivery devices, cell delivery devices, grafts, balloon occlusion devices, guidewires, filters, retrieval devices, coils, shunts, patches, clips, closure devices, embolic particles, vessel opening devices, luminal devices, cooling balloons, diagnostic devices, pressure monitoring devices, needle catheters, pacemaker leads, electro-physiology devices, diagnostic interventional devices, endoprostheses, balloon dilatation catheters, guiding catheters, support catheters, total occlusion catheters, radiation delivery catheter, drain catheters, shunt catheters, drug delivery catheter, aspiration catheters, perfusion catheters, self-expanding stent delivery systems, catheters used in heart repair, balloon-expandable stents, self-expandable stents, covered stents, bioresorbable stents, drug-eluting stents, metallic stents, polymer stents, rotobladers, arthectomy devices, coiled devices, jaw type devices, micro dissection devices, lumen re-entry devices, lumen generating devices, laser cutting devices, drilling devices, any combination thereof, and the like.

In one embodiment, the present invention includes a method for measuring particles generated from a medical device during a simulated clinical application. Such a method includes providing a platform having a medical device disposed in a medical device receptacle, pretest tubing disposed in a pretest tubing receptacle, and test tubing disposed in a test tubing receptacle. At some point, the medical device is introduced into the test tubing. A fluid is then caused to flow through the pretest tubing, past the medical device, and through the test tubing. A particle counter then counts the particles in the fluid downstream from the medical device.

In one embodiment, the present invention includes a method for measuring particles generated from a medical device during a simulated clinical application with a system adapted for conducting the method. Such a method includes the use of a system that has a platform, a pump, and a particle counter. The platform is configured for retaining at least one medical device and at least one simulated body lumen tubing. Accordingly, the platform includes the following: a medical device disposed in a medical device receptacle in the platform; pretest tubing disposed in a pretest receptacle in the platform; test tubing disposed in a test receptacle in the platform; and a junction coupling interconnecting the medical device, pretest tubing, and test receptacle. The pump is fluidly coupled to a fluid pathway that is fluidly coupled to the pretest tubing and test tubing. The particle counter can be fluidly coupled to and downstream of the test tubing or can otherwise be configured to receive the fluid. At some point, the medical device is introduced into the test tubing. A fluid is then pumped through the pretest tubing, past the medical device, and through the test tubing with a pump. A particle counter then counts the particles in the fluid downstream from the medical device. Also, the counting of particles in the fluid downstream from the test tubing can be conducted before, during, and after the medical device is introduced into the test tubing.

In one embodiment, the method includes at least one of the following: monitoring the flow rate of the fluid with a flow meter; controlling the temperature of the fluid with a temperature controller; controlling the flow rate of the fluid with a pump; counting the particles in real time; counting the particles after the fluid has been collected in a container; re-circulating the fluid; or passing the fluid past the medical device in a single pass.

In one embodiment, the method includes the following: receiving data into a computing system from at least one of the temperature controller, pump, flow meter, or particle counter; processing the data in the computing system; and transmitting instruction data from the computing system to at least one of the temperature controller, pump, flow meter, or particle counter.

In one embodiment, the method includes at least one of the following: introducing the medical device into the medical device receptacle; introducing the pretest tubing into the pretest tubing receptacle; or introducing the test tubing into the test tubing receptacle.

In one embodiment, the method includes positioning the medical device in a bent portion of the test tubing, and measuring the particles generated by the medical device positioned in at least one of the following: upstream of the bent portion of the test tubing; within the bent portion of the test tubing; or downstream from the bent portion of the test tubing.

In one embodiment, the method includes positioning the medical device in a straight portion of the test tubing that is downstream from a bent portion of the test tubing, and measuring the particles generated by the medical device positioned in at least one of the following: upstream of the bent portion of the test tubing; within the bent portion of the test tubing; or within the straight portion of the test tubing.

In one embodiment, the method includes passing the medical device through a tortuous pathway of the test tubing, and measuring the particles generated by the medical device positioned in at least one of the following: upstream of the tortuous pathway of the test tubing; within the tortuous pathway of the test tubing; or downstream from the tortuous pathway of the test tubing.

In one embodiment, the method includes introducing control particles into the fluid; determining the amount of control particles in the counted particles; and determining the amount of particles generated by the medical device.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
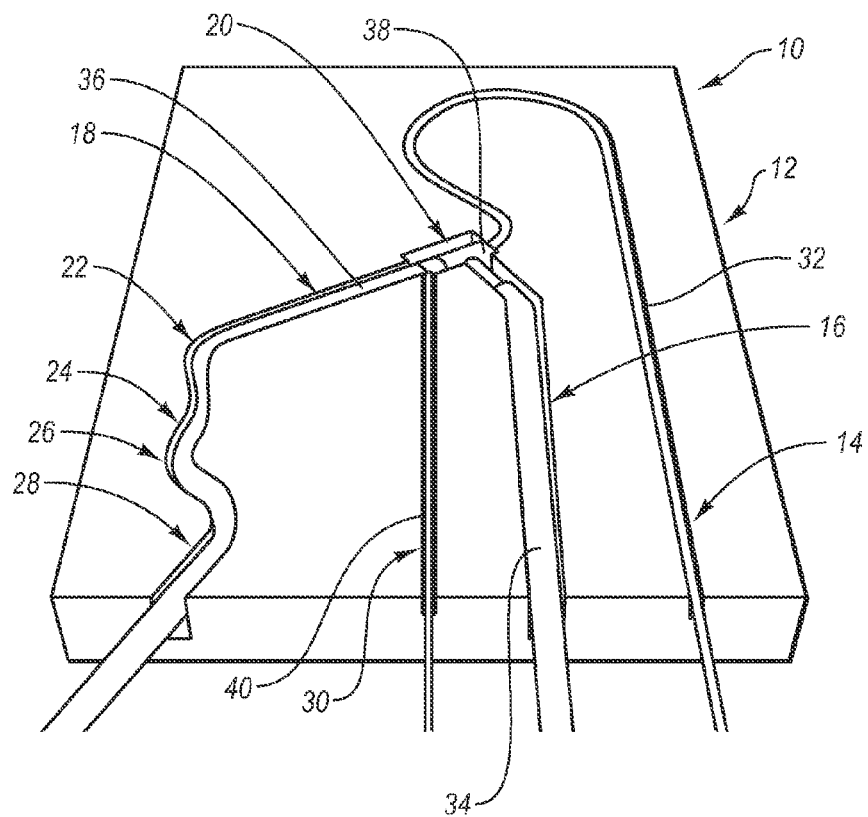
FIG. 1 is a perspective view illustrating the platform housing the medical devices, tubing for measuring particles, according to embodiments of the invention.

Generally, embodiments of the present invention include an apparatus, system, and method for measuring particles that are generated from medical devices, such as endoprostheses, catheters, or instruments, which are delivered into or utilized within the body of a patient, such as a human patient. The apparatus, system, and method are designed so as to be capable of being used to perform the real-time or steady-state measurement of particles that are generated from medical devices in a manner and condition that closely mimic the manner and condition at which the medical devices would actually be utilized within the body of the patient. Accordingly, the apparatus, system, and method are designed to study the release of particles from medical devices in a simulated clinical or surgical procedure that is closely related to the actual conditions in which the medical devices would be used. That is, the experimental conditions for measuring the particles closely approximate the actual conditions that the medical devices or instruments are used.

Accordingly, the present invention can be used to test medical devices in order to identify devices that are likely to generate particles. As such, the present invention can decrease the opportunity for particles to be generated in medical devices because those devices likely to generate particles can be tested, and medical devices that generate particles can be reconfigured to reduce particle generation or the medical device can be scrapped if the particle generation is severe. Thus, the present invention can be used to inhibit the use of medical devices that can generate particles that flow in the bloodstream, and thereby can inhibit the chances that particles can cause microembolization and the blockage of tiny tributary vessels that nourish the heart muscle. Since particles can cause distal embolization in the heart that can lead to microinfarcts or tiny heart attacks that can destroy areas of heart muscle, the present invention can be useful in preventing medical devices that generate particles that can compromise the health of the patient.

I. Introduction

In one embodiment, the present invention includes an apparatus, system, and method for determining whether a medical device generates particles and/or measuring the amount of such particles in a real-time or steady-state process. The apparatus, system, and method can simulate the conditions imposed on a medical device when being delivered or utilized within the body of a patient. As such, the apparatus, system, and method can simulate a clinical or surgical procedure so that the amount of particles generated from the medical device can be identified in a controlled setting. This allows for the amount of particles generated from the medical device to be estimated for instances of actual use in a clinical or surgical procedure. Also, the apparatus, system, and method can employ a stream of fluid that mimics or simulates blood flow so that any generated particles can be identified or measured in simulated blood flow. Thus, the present invention includes an apparatus, system, and method that measures particles generated from a medical device during a simulation of a clinical or surgical procedure.

In one embodiment, the present invention can provide the Food and Drug Administration (FDA) or other similar entity with an apparatus, system, and method that is reliable and repeatable for the measurement of particles generated by medical devices when used in a medical procedure. This can allow for the effective measurement of particles that are generated by a medical device so that safety considerations can be analyzed without introducing the medical device into a living animal. As such, reliable and repeatable experiments can be conducted to determine the safety of medical devices that are utilized within living animals without actually introducing the medical device into a living animal.

Also, an embodiment of the invention includes an apparatus, system, and method that is configured to simulate different conditions, such as temperature, pressure, stress, strain, force, and the like, to which the medical device is exposed during deployment or use within a medical procedure so that the accurate measurement of particles, and thereby prediction of generated particles, which would be generated by the use of the medical device. This includes the apparatus being configured to retain tubing that simulates a body lumen, where various strains and stresses imparted to a medical device while traversing the body lumen can be simulated. Also, the apparatus can be configured to apply stresses and strains to the medical device to simulate the stresses and strains that can be generated when a patient moves during routine daily activities. This also includes the system being configured to control fluid temperatures and pressures that simulate fluid flow in a body lumen.

Additionally, an embodiment of the present invention includes an apparatus and system dimensioned and configured to simulate the conditions of a medical procedure, which has a platform to hold the necessary medical devices, a simulated vascular system, and pumps to provided simulated fluids, each of which are intended to mimic the conditions of a medical procedure. Also, the apparatus and system can include a constricting component that can impart radial pressure onto the simulated vessels, and thereby onto the medical device disposed therein, which can simulate the forces imparted onto a medical device during routine activities.

Further, an embodiment of the present invention is an apparatus, system, and method of real-time or steady-state measurement of particles that are generated from the medical devices during use in a controlled environment in order to determine the cause and/or source from which the particles are generated in the simulation. In part, this is because the apparatus and system can be configured to simulate a real-time environment, and the method measures the particles over time. Thus, the real-time or steady-state measurements can be made to measure the generated particles over time.

In one embodiment, the system includes a fluid for use within the system. Such a fluid can simulate a body fluid. On the other hand, the fluid can be a body fluid that includes blood, blood plasma, serum, cellular components, or the like. Additionally, the system can include control particles that may optionally be included within the fluid. Otherwise, the control particles can be dry or wet, and can be injected into the fluid within the fluid pathway by being injected through in injection port.

II. Apparatus and System

The present invention includes an apparatus for measuring particles generated from a medical device during a simulated clinical application. Such an apparatus includes a platform configured for retaining at least one medical device and at least one simulated body lumen tubing. The platform includes the following: a medical device receptacle dimensioned to retain at least one medical device; a pretest receptacle dimensioned to retain pretest tubing; and a test receptacle dimensioned to retain test tubing. The test receptacle can have at least one substantially straight portion configured for straightening the test tubing when disposed therein and at least one tortuous portion configured for bending the test tubing into a bent or tortuous pathway when disposed therein. Additionally, the platform includes a junction that interconnects the medical device receptacle, pretest receptacle, and test receptacle.

In one embodiment, the present invention includes an apparatus for measuring particles generated from a medical device during simulated clinical, surgical, or interventional procedures. Such an apparatus can include any of the following: a medical device holder shaped and configured for holding or housing at least one medical device or instrument, and configured for circulating a fluid through and/or around the medical device or instrument; a circulating device configured for circulating the fluid through and/or around the medical device; a temperature regulating device configured for regulating or changing the temperature of the fluid depending on its intended purpose; a flow meter in fluid communication with the fluid such that the fluid flow rate can be measured; a monitor in communication with any of the components of the apparatus or system, and configured for monitoring the parameters or conditions associated with such components; a controller in communication with the monitor and/or any of the other components of the apparatus or system, and configured for controlling the parameters or conditions associated with such components; a measuring device configured for measuring particles generated from the medical device that are present in the fluid that passes through or around the medical device; and optionally, an alarm in communication with any of the components of the apparatus or system, and configured to sound an alert (e.g., audible, visual, electronic, etc.) or provide alarm data to the monitor and/or controller when there are undesirable changes or levels in any of the parameters or conditions of the apparatus and/or system, such as in an unacceptable change or level of temperature or flow rate. Alternatively, one or more of the components may be omitted, modulated, changed, or combined under the scope of the present invention.

In one embodiment, the present invention includes a system for measuring particles generated from a medical device during a simulated clinical application. Such a system can include a platform configured for retaining at least one medical device and at least one simulated body lumen tubing by including the following: a medical device receptacle dimensioned to retain at least one medical device; a pretest receptacle dimensioned to retain pretest tubing; a test receptacle dimensioned to retain test tubing; and a junction that interconnects the medical device receptacle, pretest receptacle, and test receptacle. The system also includes a pump that can be disposed in a position relative to the platform and that is fluidly coupled to a fluid pathway that is fluidly coupled to the pretest tubing and test tubing when disposed in the pretest receptacle and test receptacle, respectively, so as to be capable of pumping fluid through the pretest tubing and test tubing. Additionally, the system includes a particle counter that can be disposed in a position relative to the platform so as to be capable of being fluidly coupled to and downstream of the test tubing when disposed in the test receptacle. Furthermore, the system can include the components described in connection with the apparatus as described herein.

In one embodiment, the present invention includes a system for measuring particles generated from a medical device during simulated clinical, surgical, or interventional procedures. Such a system can include any of the components recited to be included in the apparatus, and can additionally include the following: a fluid having properties and characteristics which are substantially similar to bodily fluids encountered in medical procedures where the medical device is utilized, wherein the fluid is substantially free of particles; at least one medical device (e.g., medical instrument) suspected or known to be a source of particles that are generated during a medical procedure; a computing system configured to communicate with and/or control the operation of any of the components of the apparatus or system.

In one embodiment, the present invention includes an advanced system for measuring particles generated from a medical device during simulated clinical applications. Such a system includes a platform configured for retaining at least one medical device and at least one simulated body lumen tubing by having the following: a medical device receptacle dimensioned to retain at least one medical device; a pretest receptacle dimensioned to retain pretest tubing; a test receptacle dimensioned to retain test tubing; and a junction that interconnects the medical device receptacle, pretest receptacle, and test receptacle. The system also includes pretest tubing disposed in the pretest receptacle, test tubing disposed in the test receptacle, and junction coupling that couples the pretest tubing to the test tubing. Also, the system includes a fluid as described herein. Additionally, the system includes a pump fluidly coupled to a fluid pathway that is fluidly coupled to the pretest tubing and test tubing so as to be capable of pumping fluid through the pretest tubing and test tubing. Further, the system includes a particle counter capable of being fluidly coupled to and downstream of the test tubing. Furthermore, the system includes a temperature controller disposed relative to the platform at the fluid pathway so as to be thermally coupled to the fluid pathway and capable of controlling the temperature of the fluid when flowing through the fluid pathway. Furthermore, the system includes a flow meter disposed in the fluid pathway so as to measure the fluid flow rate of a fluid flowing through the fluid pathway. A computing system is in communication with at least one of the temperature controller, pump, flow meter or particle counter so as to be capable of receiving and/or transmitting data to the temperature controller, pump, flow meter, or particle counter.

In one embodiment, the particle counter can be fluidly coupled to and downstream of the test tubing. Also, the pump can be fluidly coupled to the pretest tubing and test tubing. Additionally, the temperature controller can be disposed at a fluid pathway that is fluidly coupled to the pretest tubing and test tubing, wherein the temperature controller is thermally coupled to the fluid pathway so as to control the temperature of a fluid flowing through the fluid pathway. Further, the flow meter can be disposed in the fluid pathway so as to measure the fluid flow rate of a fluid flowing through the fluid pathway. Furthermore, the apparatus can include a computing system in communication with at least one of the temperature controller, pump, flow meter, or particle counter, wherein the computing system is configured for receiving and/or transmitting data to the temperature controller, pump, flow meter, or particle counter.

In one embodiment, the pump can include at least one of a gear pump, metering pump, syringe pump, roller-pump, centripetal pump, or flow metering pump. Also, the temperature controller can include at least one of cardioplegic heat exchangers, heating devices associated with the platform, industrial heat exchangers, general heat exchangers, tube heat exchangers, batch heaters, water baths, or inductive heaters. Additionally, the flow meter can include at least one of laser meters, rotometers, bubble meters, ultrasonic meters, electrical meters, or magnetic meters. Further, the particle counter can include at least one of current displacing particle counters, or laser counters.

A. Apparatus

FIG. 1 illustrates an embodiment of an apparatus 10 configured for simulating conditions in which a medical device is deployed and used, and for measuring the particles that are generated from the medical device during the simulation. The apparatus 10 is shown to include a platform 12 configured to receive various components of the apparatus 10 and medical device system (not shown) being tested. The platform 12 can be an independent article or can be configured to be used on a bench top, which allows for the platform 12 to have various configurations, shapes, and sizes apart from those illustrated in FIG. 1. However, the platform 12 is configured and dimensioned for simulating conditions within a body, receiving tubes that simulate blood vessels or other body lumens, and receiving the medical device system being tested.

The platform 12 includes various recesses or grooves that are dimensioned for receiving apparatus components and medical device system components. As such, the platform 12 includes a medical device receptacle 14 that is configured, shaped, and dimensioned to retain a medical device. The platform 12 also includes a pretest vessel receptacle 16 that is configured, shaped, and dimensioned to retain a simulated vessel, such as a polymeric tube, that is positioned upstream from a medical device or opening in the simulated vessel that receives the medical device. Additionally, the platform 12 includes a test vessel receptacle 18 disposed downstream from the pretest vessel receptacle 16. The test vessel receptacle 18 is configured, shaped, and dimensioned to retain a simulated vessel, such as a polymeric tube, that is positioned downstream from a medical device or opening in the simulated vessel that receives the medical device. A junction 20 is disposed at an intersection between the medical device receptacle 14, pretest vessel receptacle 16, and test vessel receptacle 18.

The test vessel receptacle 18 is divided into a plurality of sections that can provide different environmental simulations for luminal deployment of the medical device. As such, the test vessel receptacle 18 includes a curved receptacle 22 (e.g., bent portion) that simulates a bend in a blood vessel or lumen. The test vessel receptacle 18 also includes a post-curve receptacle 24 (e.g., straight portion) downstream of the curved receptacle 22 that simulates the portion of a blood vessel or lumen that is disposed downstream of a bend. Additionally, the test vessel receptacle 18 includes a tight curve receptacle 26 (e.g., tortuous pathway) downstream of the post-curve receptacle 24, where the tight curve receptacle 26 has a curvature radius that is tighter in comparison with the curved receptacle 22. A post-tight curve receptacle 28 is disposed downstream of the tight curve receptacle 26, and simulates the portion of a blood vessel or lumen that is disposed downstream of a bend with a tight radius.

As shown, the platform 12 includes a secondary receptacle 30 that intersects the junction 20 so as to be coupled with the medical device receptacle 14, pretest vessel receptacle 16, and test vessel receptacle 18. However, the secondary receptacle 30 is optional. The secondary receptacle 30 is configured, shaped, and dimensioned to retain a simulated vessel or medical device. A secondary receptacle 30 can be used to simulate a branched vessel or lumen or a secondary medical device configured to operate with the medical device that is retained within the medical device receptacle 14.

During use, the platform 12 includes a catheter 32 or other deployment medical device disposed in the medical device receptacle 14. A pretest vessel 34, which can be a polymeric tube, is disposed in the pretest vessel receptacle 16. A test vessel 36, which maybe the same type or different polymeric tube compared to the pretest vessel 34, is disposed in the test vessel receptacle 18. A junction coupling 38, which can be any type of coupling (e.g., T-coupling) that can connect polymeric tubes, is disposed in the junction 20 and fluidly couples the catheter 32, pretest vessel 34, and test vessel 36. The junction coupling 38 can provide a sealed or fluid-tight coupling between the catheter 32, pretest vessel 34, and test vessel 36.

Alternatively, a tube can be disposed in the medical device receptacle 14. The tube can be configured, shaped, and dimensioned to retain a medical device. This can be beneficial for providing a fluid coupling between the pretest vessel 34 and post-test vessel 36, and with the catheter 32 or other deployment medical device.

Optionally, a secondary component 40 can be disposed in the secondary receptacle 30. The secondary component 40 can be a simulated blood vessel, lumen, or secondary medical device. The secondary component 40 can be fluidly coupled with the junction coupling 38 so as to be fluidly coupled with the catheter 32, pretest vessel 34, and test vessel 36, which can be a fluid-tight coupling.

B. System

In one embodiment, the present invention includes a system for measuring particles generated from a medical device during simulated clinical, surgical, or interventional procedures. Such a system can include any of the components recited to be included in the apparatus, and can additionally include the following: a fluid having properties and characteristics which are substantially similar to bodily fluids encountered in medical procedures where the medical device is utilized, wherein the fluid is substantially free of particles; at least one medical device (e.g., medical instrument) suspected or known to be a source of particles that are generated during a medical procedure; a computing system configured to communicate with and/or control the operation of any of the components of the apparatus or system; a temperature controller for controlling the temperature of the fluid; a pump for pumping the fluid at a rate, pressure, and/or manner similar to the pumping of a heart; an injection port for injecting particles, fluids, beads, serum, cells, or the like into the simulated vessels; a particle counter for counting the particles generated by the medical device; an alarm that can be activated when certain favorable or unfavorable operational parameters or conditions are obtained; flow meters in any of the tubes or simulated vessels; and a computing system having a transceiver for communicating with and/or controlling the various components of the system.

Figure 2:
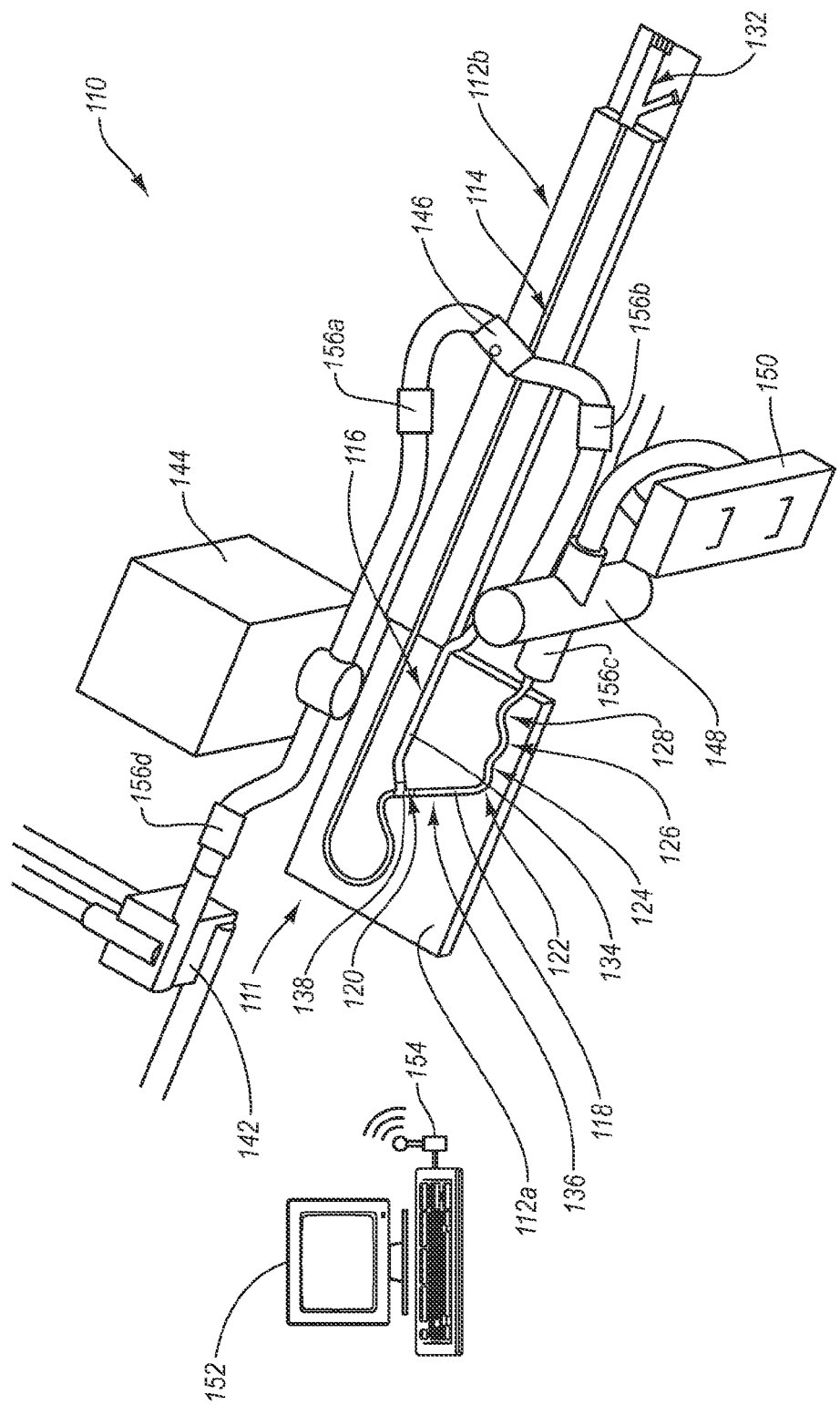
FIG. 2 is a perspective view of one set-up embodiment illustrating an arrangement of components including the heat exchanger, gear pump, injection port, pathway for saline fluids, particle counter, platform, devices, and alarm, according to embodiments of the invention.

FIG. 2 illustrates an embodiment of a system 110 configured for simulating conditions in which a medical device is deployed and used, and for measuring the particles that are generated from the medical device during the simulation. The system 110 is shown to include an apparatus 111 as described in connection with FIG. 1. As such, the system 110 includes a platform 112 configured to receive various components of the apparatus 111 and medical device system (not shown) being tested as described above. The platform 112 includes a medical device receptacle 114, pretest vessel receptacle 116, test vessel receptacle 118, and a junction 120 that are substantially similar as described in connection with FIG. 1. Additionally, the test vessel receptacle 118 is divided into a plurality of sections, such as a curved receptacle 122, a post-curve receptacle 124, a tight curve receptacle 126, and a post-tight curve receptacle 128, which are substantially similar as described in connection with FIG. 1.

Additionally, the system 110 includes a temperature controller 142 that is configured to control and/or modulate the temperature of the fluid circulating within the system 110. The fluid is circulated through the system 110 by a pump 144, which is shown to be downstream from the temperature controller 142; however, other orientations or dispositions can be used. An injection port 146 is shown to be disposed in the pretest vessel 134, which is downstream of the pump 144. A particle counter 148 is shown be disposed at the downstream end of the test vessel 136 so that any particles generated by the medical device that flow through the test vessel 136 can be counted. An alarm 150 is associated with the particle counter, and may be coupled to the fluid flow; however, the alarm 150 can be disposed at various positions. Additionally, various flow meters 156a-156d can be disposed at various positions within the system 110.

The system 110 can also include a computing system 152 for controlling the various components of the system 110. The computing system 152 can include a transceiver 154 or other communication hardware and/or software in order to be communicatively coupled to the components. For example the computing system 152 can be optically, electronically, or wirelessly coupled to the components so as to receive and transmit data therebetween.

During use, the platform 112 includes a catheter 132 disposed in the medical device receptacle 114. A pretest vessel 134 is disposed in the pretest vessel receptacle 116, and a test vessel 136 is disposed in the test vessel receptacle 118. A junction coupling 138 is disposed in the junction 120 and fluidly coupled to the catheter 132, pretest vessel 134, and test vessel 136. A fluid source (not shown) can provide the fluid to the temperature controller 142, which is then pumped by the pump 144 through the system 110 at a rate, pressure, and/or manner similar to the pumping of a heart. The fluid is then pumped through the pretest vessel 116 and through the injection port 146. Optionally, various substances, such as those described herein, can be introduced into the fluid via the injection port 146. The fluid then continues through the pretest vessel 116 and into the junction coupling 138 where it enters the test vessel 136. While passing through the test vessel 136, the fluid can pass through the various features disposed therein and past the medical device disposed therein that is being tested for particle generation. After the fluid passes the medical device, the particles that are carried by the fluid are counted by the particle counter. The flow meters 156a-156d that are disposed at various positions within the fluid path in the system 110 record the flow rate of the fluid and provide flow data to the computing system 152. The computing system receives the flow data and transmits pump instructions to the pump 144 via the transceiver 154 so that the flow rate can be modulated as needed or desired.

C. Apparatus and System Components

In one embodiment, the apparatus and system can include a delivery means for delivering the medical device. Such a delivery means can be a secondary medical device for facilitating the delivery of the primary medical device that is being studied for particle generation during the simulated clinical application. However, the secondary device can also be studied. The delivery means can be automated or passive depending on the standard or routine means of delivering or deploying the primary medical device during actual use. For example, the delivery means can include a guide catheter for delivering the medical device, which can include manual or automated components for delivering the medical device via the catheter.

In one embodiment, the apparatus and/or system can include a pretest particle measuring device that is configured and oriented so as to be capable of measuring particles in the circulated fluid at a stage where the primary device has been delivered through the secondary device. This can also include a position after the primary device has been deployed substantially to the intended location during the simulated clinical application. Also, this includes particle measurements while the primary device is still disposed within the secondary device.

In one embodiment, the apparatus and/or system can include a post-track particle measuring device that is configured and oriented so as to be capable of measuring the circulated fluid for particles at a post-track stage where the primary device is delivered outside of the secondary device to its intended location during the simulated clinical application. As such, the primary particle counter can function as the measuring device, or another measuring device can be utilized. Multiple measuring devices can be beneficial for measuring particles at multiple locations within the apparatus and system.

The particle counter can be any apparatus configured for measuring the amount, size, and/or distribution of particles in the fluid. Such a particle counter can include standard particle counters, current displacing particle counters, Coulter® method counters, laser counters, and manual counting. The particles that are generated from the medical device in the apparatus at various stages during the simulated procedure are identified as being present and/or measured by the particle counter, where the particle counter is usually oriented downstream from the medical device. The particle counter can be configured for measuring the particles in the fluid in real-time or steady-state conditions while the fluid is circulating through the system. Also, the particle counter can be a batch-type counter that measures the particles after the fluid is collected. It can be beneficial for the particle counter to include electronics that can generate particle data. Also, it can be beneficial for the particle counter to be configured for communicating with the computing system so that particle data can be provided thereto. The particle counter can include any subcomponents that can measure particles, can record particle data, and can transmit particle data to the computing system.

In one embodiment, the apparatus and system can include an injecting apparatus for administering a fluid into the simulated vessels. The injecting apparatus can be configured as a syringe that is either manual or automated. Such an injecting apparatus is well known in the art.

In one embodiment, the system can include a fluid that has a known particle(s) count and/or size distribution. This can include a fluid having a known amount of particle and/or known particle size distribution to act as a control. Also, this can include another fluid that is different than the control. For example, the fluid can be a water-based liquid that simulates a body fluid, such as blood. Also, the fluid can be blood, blood plasma, serum and/or cellular components. Additionally, the fluid can be obtained by being directly withdrawn from a mammal or other animal that is connected or unconnected to the system. Thus, various types of fluids can be employed in the present invention.

The primary medical device being deployed and studied for particle generation can be an endovascular device or instrument. As such, the primary medical device can be selected from the group consisting of stents, catheters, balloons, drug and/or cell delivery devices, catheters, grafts, balloon occlusion devices, guidewires, filters, retrieval devices, coils, shunts, patches, clips, closure devices, spheres, embolic particles, vessel opening devices, lumenal devices, laser/cooling/chilling catheters/balloons devices, cooling balloons, diagnostic devices, pressure monitoring devices, needle catheters, pacemaker leads, electro-physiology devices, diagnostic interventional devices, and implants, and any practicable combinations thereof.

For example, the stents can include balloon and self-expandable stents, covered stents, bioresorbable stents, single or multiple drug delivery/coated stents, metallic stents, polymer stents, and any practicable combination thereof. Examples of suitable stents which may be utilized in accordance with the device and methods of the invention are shown and described in U.S. patent application Ser. No. 10/430,644 filed May 6, 2003 entitled "Endoprosthesis Having Foot Extensions" the entity of which is herein incorporated be reference. However, any stent can be studied.

For example, the catheters can include balloon dilatation catheters, guiding catheters, support catheters, total occlusion catheters, radiation delivery catheter, drain catheters, shunt catheters, drug delivery catheter, aspiration catheters, perfusion catheters, and catheters used in heart repair, and any combination thereof.

Additionally, the medical device can be a vessel opening device. Such vessel opening devices can include rotoblader, arthectomy devices, coiled devices, jaw-type devices, micro dissection devices, lumen re-entry devices, lumen generating devices, laser cutting devices, and drilling devices, and any practicable combination thereof.

Also, the medical device can be a drug delivery device. Drug delivery devices that are deployed into a body lumen are well known in the art and can include drug delivery balloons, catheters, implants, drug-eluting stents, drug delivery devices utilized in mammalian vasculature, and the like. Additionally, the primary medical device can be multi-component medical device system. For example, a multi-component medical device system includes a filter and stent delivery system. It is appreciated to one skilled in the art that one or more medical devices can be utilized with the invention.

The platform for holding or housing at least one device and fluid can be a platform having indentations (e.g., receptacles for simulated vasculature and medical devices). Such indentations are dimensioned and configured for devices, instruments, tubing, fluids, and/or items to hold the medical devices. The platform can be comprised of various materials, such as plastics, metals, ceramics, and composites. It can be beneficial for the material to be able to change temperature and/or hold a temperature. In part, this allows a temperature controller to control the temperature of the fluid and allow the fluid to retain the set temperature throughout the experiment. Also, the platform can be thermally coupled with a heater that can be used to adjust or maintain the temperature of the platform.

In one embodiment, at least one of the medical device receptacle, pretest receptacle, or test receptacle includes a means for securing the medical device, pretest tubing, or test tubing to the platform. Accordingly, the means for securing is selected from the group consisting of a fastener, lip, adhesive, top platform, housing, cover, and/or contoured receptacle walls. Also, the medical device, pretest tubing, and test tubing can be disposed in their respective receptacles. Moreover, the pretest tubing can be fluidly coupled with the test tubing via a junction coupling disposed in the junction.

Various types of tubes can be used to simulate a body lumen. This can include any type of flexible or rigid tubing. The tubing can be elastomeric so as to simulate a blood vessel. This can include the tubing being rubber, polymeric, or the like. Also, the type of tube can be modulated to simulate different body lumens. For example, the test vessel can be polyvinylalcohol (PVA) tubing of appropriate diameter, with an inner diameter substantially equal to the labeled diameter of the medical device being tested.

The junction coupling can be configured similarly as the tubes. However, the number of ports in the junction coupling can be modulated to accommodate different numbers of simulated vessels and/or medical devices. For example, the junction coupling can be comprised of a rigid plastic that can be fluidly coupled with the simulated vessels and medical device to provide a fluid tight seal.

The injection port coupling can be configured similarly as the tubing and the junction coupling. Also, the injection port coupling can include a needle-piercable or other piercable membrane or member that can allow fluids and/or particles to be injected into the fluid stream. As such, the injection port coupling can have a portion that is configured to be re-sealable after injection. Injection ports are well known in the art.

The pump can be any type of fluid pump that is configured for circulating the fluid through the tubing and/or simulated vessels. As such, the pump can be any type of gear pump, metering pump, syringe pump, roller-pump, centripetal pump, gravity pump, flow metering pump, pulsing pump, heart beat-replicating pump, and the like. The pump can be configured for either continuous fluid re-circulation or single one-pass through the system. Also, the pump can pump the fluid so as to simulate the flow of blood from a beating heart. Additionally, the pump can be configured with electronics that enable communication with the computing system. This can allow the pump to receive pump data from the computing system in order to change the pump rate, and can allow for the pump to transmit pump data to the computing system. Optionally, the circulation of fluids could be by gravity, or intermittent circulation, or not circulating at all.

The fluid flow rate monitoring apparatus can be any device that can be used for monitoring the flow rate of the circulating fluid through the system. Such a monitoring apparatus can include any type of flow meters, flow meter having electronics, flow meters having an alarm for alerting changes in flow rate of the fluid, and flow meters with feed back to control flow at pump. The flow meter can be selected from laser meters, photometers, rotometers, bubble meters, ultrasonic meters, electrical meters, magnetic meters, and the like. Although a feedback mechanism is optional, an example of one uses an alarm as a feedback mechanism. It can be beneficial for the flow meter to include electronics that can generate flow rate data. Also, it can be beneficial for the flow meter to be configured for communicating with the computing system so that flow rate data can be provided thereto.

The temperature controller can be any device that can measure and/or control the temperature of the fluid. This includes the ability to heat and/or cool as well as maintain the temperature of the fluid. The temperature controller can include cardioplegic heat exchangers, heating devices associated with the platform, industrial heat exchangers, general heat exchangers, tube heat exchangers, batch heaters, water baths, heaters, coolers, inductive heating, and the like. It can be beneficial for the temperature controller to include electronics that can generate fluid temperature data. Also, it can be beneficial for the temperature controller to be configured for communicating with the computing system so that fluid temperature data can be provided thereto. However, the temperature controller can be optional.

The temperature controller can include any subcomponents that measure temperature, record temperature data, transmit temperature data to the computing system, receive temperature regulating data from the computing system, and change the temperature of the fluid. This can include the temperature controller having a thermocouple, a heating and/or cooling element, and electronics and hardware configured to transmit and receive temperature-related data. As such, the temperature of the fluid is regulated or changed by the temperature regulating apparatus. The temperature controller can be disposed at various positions within the system, and a plurality of temperature controllers can be used. Additionally, a plurality of thermocouples can be oriented in the system to measure the temperature at various locations, where the thermocouples can provide temperature data to the temperature controller and/or the computing system.

The alarm can be any device that can provide a warning to a user or to the apparatus or system. As such, the alarm can include electronic and communication subcomponents that can receive data, generate alarm data, and communicate data with the computing system. The alarm can be configured to provide the warning in the event that the temperature, fluid flow rate, or other parameter reaches a level or undesirable condition. For example, the alarm can be activated when the apparatus exhibits any undesirable flow rates.

The computing system can include any type of computer that can be controlled or programmed to implement the experiments described herein. As such, a standard computer or custom computer can be used. The computing system can include hardware and software for being programmed, receiving data, and transmitting data to the various components. Also, the computing system can include a transceiver for transmitting and receiving data. Computing systems are well known in the art.

Additionally, the apparatus and system can include a compression sleeve that fits partially or circumferentially around the tubing of the simulated vessels. The compression sleeve can be configured to selectively apply radial pressure to the tubing so as to simulate the forces that can be applied to a medical device disposed in a body lumen during routine daily activities. The compression sleeve can be configured to expand and contract so as to change the amount of compression applied to the tubing. Such compression can be automated or manual. The compression sleeve can be configured similarly to the compression sleeve of a blood pressure cuff.

III. Methods of Measuring Particle Generation

The present invention includes methods for determining whether a medical device generates particles and/or for measuring the amount of particles that are generated in a simulated clinical application. Such methods can include any combination of the various steps or stages of determining particle generation and/or measuring the particles that are described herein.

In one embodiment, the methods for determining particle generation and/or measuring the amount of particles generated from a medical device during simulated clinical applications can include providing any combination of the following components: providing a desired fluid having properties and characteristics which are substantially similar to bodily fluids encountered in clinical applications of the devices or instruments, wherein the fluid is substantially free of particles; providing at least one medical device that is capable of being the source of generating particles during simulated or real clinical applications; providing a platform or holding apparatus to hold or house at least one medical device and fluid during the simulation; providing a pump or circulating apparatus for circulating the fluid through the system during the process of conducting the method and controlling the fluid flow rate; providing a temperature controller or temperature regulating apparatus for controlling the temperature of the fluid and/or platform depending on its intended purpose; providing a flow meter to monitor the flow rate of the fluid, providing a particle counter or other particle detecting and/or measuring apparatus for detecting the presence and/or measuring the amount of particles in the fluid; and optionally providing an alarming apparatus to alert when undesirable changes in flow rate or other parameter are detected.

In one embodiment, the present invention includes a method for measuring particles generated from a medical device during a simulated clinical application. Such a method includes the use or providing a platform having a medical device disposed in a medical device receptacle, a pretest tubing disposed in a pretest tubing receptacle, and a test tubing disposed in a test tubing receptacle. The medical device is introduced into the test tubing. A fluid is then caused to flow through the pretest tubing, past the medical device, and through the test tubing. A particle counter then counts the particles in the fluid downstream from the medical device.

In one embodiment, the present invention includes a method for measuring particles generated from a medical device during a simulated clinical application with a system adapted for conducting the method. Such a method includes the use of or providing a system that has a platform, a pump, and a particle counter. The platform is configured for retaining at least one medical device and at least one simulated body lumen tubing. Accordingly, the platform includes the following: a medical device disposed in a medical device receptacle in the platform; pretest tubing disposed in a pretest receptacle in the platform; test tubing disposed in a test receptacle in the platform; and a junction coupling interconnecting the medical device, pretest tubing, and test receptacle. The pump is fluidly coupled to a fluid pathway that is fluidly coupled to the pretest tubing and test tubing. The particle counter is fluidly coupled to and downstream of the test tubing. The medical device is introduced into the test tubing. A fluid is then pumped through the pretest tubing, past the medical device, and through the test tubing with a pump. A particle counter then counts the particles in the fluid downstream from the medical device. Also, the counting of particles in the fluid downstream from the test tubing can be conducted before, during, and after the medical device is introduced into the test tubing.

In one embodiment, the methods of the invention can include various protocols for implementing the detection of particles and/or measuring the amount of generated particles. Accordingly, the methods can include any combination of the following: circulating the fluid through the medical device by a circulating apparatus as appropriate depending on the simulated clinical applications; regulating the fluid temperature with a temperature controller; monitoring the fluid flow rate with a flow meter; and measuring particles in the circulating fluid at various stages during the simulated clinical applications for determining the amount of particles generated by the medical device(s). Optionally, the methods can include the alarm being activated so as to provide an alert when undesirable changes in flow rate or other operational parameter occur.

In one embodiment, the methods may determine the presence of and/or measure the amount of particles that are generated when a secondary medical device is utilized for delivering the primary medical device. Such methods may be conducted by providing a delivery means or secondary medical device for facilitating the delivery of a primary medical device during the simulated clinical application. Also, the methods may determine the presence of and/or measure the amount of particles that are generated with and without the use of a secondary medical device to delivering the primary medical device. The secondary medical device can be a guidewire, guide catheter, and the like.

In one embodiment, the methods may determine the presence of and/or measure the amount of particles at a specific stage with respect to the location of the medical device during deployment before, during, and/or after deployment of the medical device. This can also include methods that include the use of a secondary medical device to deploy the primary medical device. As such, the particles generated at any stage of deployment can be detected and/or measured. For example, the particles that are generated can be detected and/or counted by measuring the circulated fluid for particles at any stage of deployment when the primary device is delivered through the secondary device to its intended location during the simulated clinical application, which includes measurements taken while the primary medical device is at any stage within or associated with the secondary medical device. In another example, the particles that are generated can be detected and/or counted by measuring the circulated fluid for particles at a post-track stage where the primary medical device is delivered and deployed outside of the secondary medical device to its intended locations during the simulated clinical application.

In one embodiment, the method includes at least one of the following: monitoring the flow rate of the fluid with a flow meter; controlling the temperature of the fluid with a temperature controller; controlling the flow rate of the fluid with a pump; counting the particles in real time; counting the particles after the fluid has been collected in a container; re-circulating the fluid; or passing the fluid past the medical device in a single pass.

In one embodiment, the method includes the following: receiving data into a computing system from at least one of the temperature controller, pump, flow meter, or particle counter; processing the data in the computing system; and transmitting instruction data from the computing system to at least one of the temperature controller, pump, flow meter, or particle counter.

In one embodiment, the method includes at least one of the following: introducing the medical device into the medical device receptacle; introducing the pretest tubing into the pretest tubing receptacle; or introducing the test tubing into the test tubing receptacle.

In one embodiment, the method includes positioning the medical device in a bent portion of the test tubing, and measuring the particles generated by the medical device positioned in at least one of the following: upstream of the bent portion of the test tubing; within the bent portion of the test tubing; or downstream from the bent portion of the test tubing.

In one embodiment, the method includes positioning the medical device in a straight portion of the test tubing that is downstream from a bent portion of the test tubing, and measuring the particles generated by the medical device positioned in at least one of the following: upstream of the bent portion of the test tubing; within the bent portion of the test tubing; or within the straight portion of the test tubing.

In one embodiment, the method includes passing the medical device through a tortuous pathway of the test tubing, and measuring the particles generated by the medical device positioned in at least one of the following: upstream of the tortuous pathway of the test tubing; within the tortuous pathway of the test tubing; or downstream from the tortuous pathway of the test tubing.

In one embodiment, the methods can be conducted with control particles. As such, the fluid can be modulated to include control particles that can be compared against unknown particles that are generated by the medical device. The control particles can be well characterized particles that are known to have a selected size, size distribution, shape, and the like. Also, the control particles can be a known amount of particles. Moreover, the control particles can be well characterized in the manner in which they flow within the fluid. As such, methods using the control particles can be conducted by injecting the control particles into the fluid and taking particle measurements, before, during, and after the control particles are disposed within the circulating fluid. Also, the fluid itself can be well characterized and have a known amount of particle and/or known particle size distribution to act as a control.

In one embodiment, the method includes introducing control particles into the fluid; determining the amount of control particles in the counted particles; and determining the amount of particles generated by the medical device.

In one embodiment, the methods can be conducted by using a fluid having a known particle(s) count and/or size distribution that is different than the control. These known particles can operate as secondary controls. Also, the controls can be positive and negative controls. In any event, the secondary control particles can provide particle generation data that is different from data obtained from the primary controls so as to determine whether different particles in the fluid can modulate the particle generation from the medical device.

In one embodiment, the fluid can be a body fluid obtained from an animal, such as a mammal. Accordingly, the fluid can be comprised of blood, blood plasma, serum and/or cellular components. Also, other body fluids can be used depending on the nature of the medical device and the environments in which the medical device is employed. Additionally, the body fluid can be directly withdrawn from an animal that is connected to the system so that the body fluid flows directly into the system. Alternatively, the body fluid can be obtained from an animal that is not connected to the system.

An example of a method using the apparatus and system of the present invention is provided. The simulated vessel tubing can be disposed within the receptacles illustrated and described with respect to FIGS. 1 and 2. An Asahi Prowater guidewire (180 cm, Straight Tip) can be inserted through the medical device tubing that is fit into the medical device receptacle and tracked therethrough to the test vessel. For example, the guidewire can be inserted through a Touhy-borst of a Rotating Haemostatic Valve (RHV) and tracked to the PVA test vessel. The guidewire can be positioned in the PVA test vessel at about 2 cm beyond the stent deployment side. The guide catheter can then be deployed via the guidewire as is standard in the art.

The distal end of the PVA test tubing can be connected to the inlet of an HIAC flow particle sensor via a barbed connector and tubing. The HIAC flow particle sensor can be factory calibrated to a flow rate of 100 ml/min (±10%). The flow rate can be monitored (e.g., continual monitoring) by connecting the outlet of the HIAC flow particle sensor to an alarm flow meter. The alarm flow meter can trigger an alarm when the flow rate deviates outside the range of 90-110 ml/min. Usually, the only allowable time for the flow rate to deviate outside of this range is during the expansion of the stent to rate of burst pressure (RBP) when flow is restricted distal to the balloon. The particle counter can be configured to not count during this time, but once the balloon is deflated the flow rate can return to about 100 ml/min, and the particle counts may recommence. The measurement of particles at any point can be recorded in a data collection sheet. The effluent from the flow meter can be discarded into a waste container.

The stent can be loaded over the guidewire and carefully introduced into the guide catheter through the fully opened RHV. The stent can be pre-tracked through the guide catheter until it exits out of the distal end of the guide catheter, and the stent can be positioned in a clear, straight part of the PVA tubing. After the particle count is stabilized (e.g., less than 1-2 particles of 10 and 25 um are counted every 10 seconds), a measurement of the differential particle count for the pre-tracking step can be recorded onto the data collection sheet. The particles generated during this step can represent the particles generated during pre-tracking. This is one of the various stages (e.g., pre-tracking stage) during the simulated clinical application where the particles are measured in the circulating Isotonic fluid.

In another stage, the stent can be tracked through the PVA test vessel and positioned in a tortuous curve. After the particle count has stabilized (e.g., less than 1-2 particles of 10 and 25 um are counted every 10 seconds), a measurement of the differential (e.g., 10-25 um and >25 um) particle count is recorded in the data collection sheet. The particles generated during this step or stage, represent the particles generated during post-tracking of the stent.

Another stage where particles can be measured during a simulation is in the Rate Burst Pressure (RBP). In the simulation, the stent can be expanded and held for 20 seconds and then deflated, and then the particle count allowed to stabilize and reach baseline levels. A measurement can be taken of the differential particle counts, which is recorded in the data collection sheet. The particles generated during this step represented the particles generated during expansion to RBP stage.

EXAMPLES

The examples described herein were conducted with the apparatus and system substantially as illustrated and described with respect to FIGS. 1 and 2. Accordingly, a 5F-JL4 VistaBriteTip guide catheter is inserted into the medical device receptacle and simulated polyvinylalcohol vessel tubing are disposed within the test vessel receptacles. The guide catheter and simulated vessels are connected via the junction connector. An Asahi Prowater guidewire (180 cm, Straight Tip) is inserted through the guide catheter and tracked therethrough to the test vessel. The guidewire is inserted through a Touhy-borst of a Rotating Haemostatic Valve (RHV) and tracked to the PVA test vessel. The guidewire is positioned in the PVA test vessel at about 2 cm beyond the stent deployment site. The distal end of the PVA test tubing is connected to the inlet of an HIAC flow particle sensor via a barbed connecter and tubing. The HIAC flow particle sensor is factory calibrated to a flow rate of 100 ml/min (±10%). The flow rate is monitored (e.g., continual monitoring) by connecting the outlet of the HIAC flow particle sensor to an alarm flow meter. The alarm flow meter will trigger an alarm when the flow rate deviates outside the range of 90-110 ml/min. Usually, the only allowable time for the flow rate to deviate outside of this range, is during the expansion of the stent to rate of burst pressure (RBP) when flow is restricted distal to the balloon. The particle counter does not count during this time, but once the balloon is deflated the flow rate can return to about 100 ml/min, and the particle counts may recommence. The effluent from the flow meter is discarded into a waste container. The stent is loaded over the guidewire and carefully introduced into the guide catheter through the fully opened RHV. The stent is pre-tracked through the guide catheter until it exits out of the distal end of the guide catheter, and the stent is positioned in a clear, straight part of the PVA tubing. After the particle count is stabilized (e.g., less than 1-2 particles of 10 and 25 um are counted every 10 seconds), a measurement of the differential particle count is recorded onto the data collection sheet.

The foregoing model used was verified by injection with particle standards of known sizes and concentrations before and after product testing. This ensured that all the particles entering and exiting the system were correctly counted by the HIAC flow sensor.

The detection of particles and/or measurement of the amount of particles were competed in three stages that simulate common stages in deploying a medical device in a clinical application. The three steps (e.g., stages) where particle measurements were taken are summarized in Table 1. The term "step" and "stage" can be interchangeable in most embodiments of the invention.

TABLE 1

| Step | Sample Type | Description |
|---|---|---|
| 1 | Pre-track through the Guide Catheter. | Particle counts generated while pre-tracking the SDS through the guide catheter and into a straight section of the PVA |
| 2 | Post-track through the PVA vessel. | Particle counts generated while tracking of the SDS through the PVA vessel to deployment site |

TABLE 1-continued

| Step | Sample Type | Description |
|---|---|---|
| 3 | Deployment to Rated Burst Pressure (RBP). | Particle counts generated during post dilation of stent to Rated Burst Pressure |

The experiments compared the total number of particles released by three SDSs with similar competitor devices. Testing was completed on the units listed in Table 2, which summarizes the test article, size, and pattern of test articles.

TABLE 2

| Test Article | Size | Pattern |
|---|---|---|
| Catheter A | 2.5 mm × 8 mm | J |
| Catheter B | 3.0 mm × 15 mm | N |
| Catheter C | 4.0 mm × 38 mm | K |
| Competitive Catheter A | 3.0 × 15 mm | — |
| Competitive Catheter B | 3.0 × 18 mm | — |
| Competitive Catheter C | 3.0 × 15 mm | — |

Competitor catheter C has a hydrophilic coating on it, which is a potential source of particles.

Example 1

An experiment was conducted to determine the amount of particles that are generated by guidewire and delivery catheters (e.g., on which the stent is delivered) to the total catheter/stent particle count. The evaluation of the total number of particles released by the stent delivery system (SDS) should be less than the USP 788 standard. This experiment quantitated the total number of particles that are generated from the SDS after the following steps (stages): pre-track through the guide catheter, post-track through the simulated vessel, polyvinylalcohol (PVA), and deployment being contricted or unconstricted to Rated Burst Pressure (RBP). This experiment also quantitated the number of particles that are generated by competitor delivery catheters on which the stent is mounted, and evaluated on the contribution of the competitor's delivery catheter to the total of the particle count.

The simulated clinical application in this experiment pertains to coronary test system, where the experimental setup was substantially as described above. Briefly, the medical device receptacle was lined with a 5F-JL4 VistaBriteTip guide catheter. A Rotating Haemostatic valve (RHV) was attached to the proximal port of the guide catheter. The injection port of the RHV was capped. The Touhy-Borst arm of the RHV was used to introduce the guide wire and SDS. The distal tip of the guide catheter was inserted into the appropriate introducer arm of the junction coupling. Isoton fluid (0.09% NaCl particle free buffered saline) was pre-heated via the use of a cardioplegic heat exchanger. The Isoton fluid exiting the heat exchanger was maintained at 37° C., via re-circulating water heated to 42° C., which also flows through the heat exchanger. This higher temperature maintains the Isoton fluid within the system to about 37° C.±2° C. The Isoton fluid was connected to a volume displacement pump set for a displacement volume of 100 ml/min via polyethylene tubing. The Isoton fluid inlet tubing from the pump was connected to an injection port for introducing particle standards (e.g., controls), and further connected to the junction coupling (e.g., a T-connecter). Additionally, the Isoton fluid tubing was continued from the T-connector at the junction through the tortuous test path receptacle of the platform, and the distal end of the tubing was firmly inserted into the second arm of the introducer.

The means for measuring (e.g., counting) particles is an HIAC flow particle counter, more specifically, an optical particle counter. In this particle counter, the particles interrupt light energy from a laser diode. A photodiode, with its associated electronics, converts the shadows into electrical pulses. The pulse height is proportional to particle size. The pulses are counted and their intensity is measured for particle size. Results are displayed as particles count in the specified size channel. The sensor is calibrated to a flow rate of 100 ml/min.

This experiment compared the total number of particles released by Applicants' SDS's with similar competitor devices. Testing was completed on the following units listed in Table 2 above. The test setup was verified with 15 (PHARM-TROL™ Particle Count Controls, Cat #CS3800-15) and 30 um particle standards (COUNT-CAL Particle Size Standards, Cat #CC30-PK) of known concentrations from Duke Scientific Corporation as listed in Table 3.

TABLE 3

| Particle Size | Nominal Diameter | Concentration | Lot Number | Expiration Date |
|---|---|---|---|---|
| 15 um | 15.0 um ± 0.1 um | 3800 particles/ml ± 10% | 28880 | March 2007 |
| 30 um | 30.10 um ± 0.22 um | 3000 particles/ml ± 10% | 29160 | August 2006 |

All of the following steps were performed inside of a Laminar Airflow Hood: rotate the 15 um and 30 um standard bottles well to reconstitute the spheres; withdraw 1 ml of each standard into 2 micro syringes and dispense out to waste; carefully withdraw 1 ml of each of the 15 um & 30 um size particle standards with the same relevant micro syringes; slowly inject the particle standards, one immediately after the other, into the injection port taking care to ensure that the flow rate stays within the 100±10% ml/min range; when the injection is complete remove the syringe from the port; measure the differential particle output on the particle counter for both sizes introduced and record the particle measurements in the data sheets; and repeat the above protocol twice more to get a total of 3 injections before and after testing commences each day. The total number of particles recovered/measured from the path is listed in Table 4.

TABLE 4

| Volume Injected | Total Particles In The Injected Volume | Acceptable Range Of Particles Recovered From The Path |
|---|---|---|
| 1 ml of 15 um | 3800 particles ± 10% | 3420 to 4180 particles |
| 1 ml of 30 um | 3000 particles ± 10% | 2700 to 3300 Particles |

All subsequent steps were performed inside of a Laminar airflow hood. New PVA tubing was used for each test device. Table 5 outlines the size of the PVA tubing, tubing diameters and RBP that was utilized for each group of test devices.

TABLE 5

| Test Article | Size | Inner Diameter of PVA Tubing | RBP To Be Used (As Per IFU) |
|---|---|---|---|
| Catheter A | 2.5 mm × 8 mm | 2.5 mm | 14 |
| Catheter B | 3.0 mm × 15 mm | 3.0 mm | 14 |
| Catheter C | 4.0 mm × 38 mm | 4.0 mm | 14 |
| Competitive Catheter A | 3.0 x 18 mm | 3.0 mm | 16 |
| Competitive Catheter B | 3.0 x 15 mm | 3.0 mm | 16 |
| Competitive Catheter C | 3.0 x 15 mm | 3.0 mm | 14 |

Preparation of the balloon lumen of the SDS was conducted substantially as follows: a 20 cc syringe was filled with water approximately ¼ full; all the air was purged from the syringe; the syringe was attached to the balloon inflation port of the catheter; the syringe and proximal end of the catheter was held upright, the plunger on the syringe was drawn back to create a vacuum, and the air was drawn out of the catheter; when air ceased to bubble from the hub into the syringe, the plunger was slowly released and the water was permitted to enter the catheter for the control; and a flushing device and Isoton fluid was utilized to flush the guidewire lumen of the stent delivery system. The flushing device is the means for injecting a fluid having a known particle, which is the control of the experiment. The tortuous model was flushed with sufficient Isoton fluid until baseline levels are established.

This measurement of particles was recorded in a data collection sheet. The SDS was loaded over the guidewire and carefully introduced into the fully opened RHV, and then pre-tracked through the guide catheter until the SDS was exited out of the distal end of the guide catheter and the stent was positioned in the clear straight part of the PVA tubing (e.g., test vessel). After the particle count has stabilized (e.g., less than 1-2 particles of 10 and 25 um are counted every 10 seconds), a measurement of the differential particle count for the pre-tracking step was recorded onto the data collection sheet. The particles generated during this step represent the particles generated during pre-tracking. This is one of the various stages (e.g., pre-tracking stage) during the simulated clinical application where the particles are measured in the circulating Isoton fluid.

In another stage, the stent is tracked through the PVA vessel and positioned in a tortuous curve. After the particle count was stabilized (e.g., less than 1-2 particles of 10 and 25 um are counted every 10 seconds), a measurement of the differential (10-25 μm and >25 um) particle count was recorded in the data collection sheet. The particles generated during this step (stage) represented the particles generated during post-tracking of the SDS.

Another stage where particles are measured during this simulation is the Rate Burst Pressure stage. In the simulation, the stent is expanded and held for 20 seconds. The stent is deflated and then there was a wait for the particle count to stabilize and reach baseline levels. A measurement was taken of the differential particle counts and recorded in the data collection sheet. The particles generated during this step represented the particles generated during expansion to RBP stage.

The cumulative particle count generated during the steps (stages) represented the total number of particles generated per device. The total number of particles generated per stent/device for the above stent should meet the following USP 788 standard summarized in the Table 6.

TABLE 6

| USP 788 Acceptable Particle Limit | Between 10-25 um | >25 um |
|---|---|---|
|  | 6000 | 600 |

Example 2

An experiment was conducted to measure particle generation of a drug coated, balloon expandable RX coronary SDS. The experiment quantitated the total number of particles that were released by catheters A-C, and competitive catheters A and B. This experiment included the same three steps (stages) where particle measurements were taken and are summarized earlier in Table 1. This experiment also quantitated the number of particles generated by competitive catheters.

Briefly, a test model was validated with 15 um and 30 um particle standards before and after start of testing. Table 2 above summarizes the test matrix listing the patterns and sizes of each unit.

The total number of particles generated by catheters A-C were similar to that of Competitive Catheter A and lower than that of Competitive Catheter B. All Catheters A-C patterns tested passed the USP 788 standard. New PVA tubing was used for each test device. Table 5 above outlines the size of the PVA tubing and RBP that was utilized for each group of test devices.

The units were tested and the test models were validated as per the same procedures as outlined in Example 1. The following deviations were made to the protocol: PVA tubing of 3.0 mm ID was used for Catheters A-C sizes 2.5×8 mm and 4.0×38 mm as 2.5 mm ID and 4.0 mm ID PVA tubing was not available. These sizes are currently being manufactured and correct sizes will be used in all future studies. An RBP of 16 atmospheres was used for Catheters A-C sizes 2.5×8 mm and 3.0×15 mm instead of 14 atmospheres.

Figure 3:
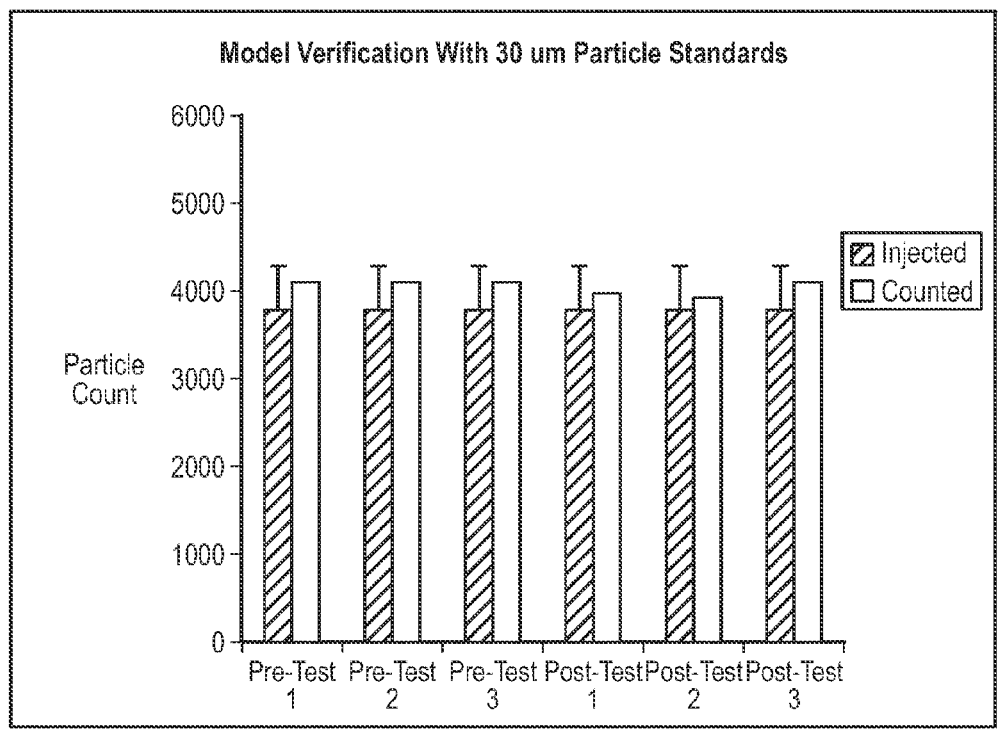
FIG. 3 is a graph showing model verifications utilizing 15 um particle standards, according to embodiments of the invention.
Figure 4:
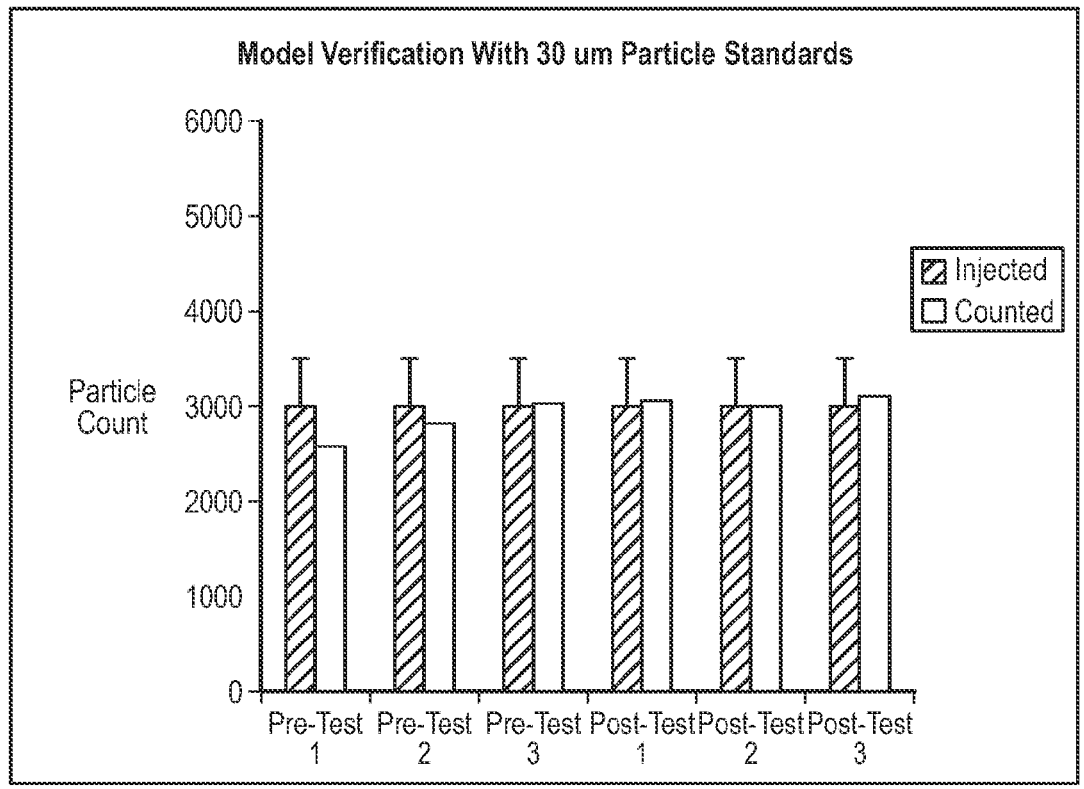
FIG. 4 is a graph showing model verifications utilizing 30 um particle standards, according to embodiments of the invention.

Model verifications with particle standards are shown in FIGS. 3 and 4. The tortuous model used was verified with 15 and 30 um particle standards of known concentrations before and after the start of device testing. Table 7 is the values of the bars in the FIGS. 3 and 4.

TABLE 7

| Validation Step | Number of 15 um Particles Injected | Number Counted | Number of 30 um Particles Injected | Number Counted |
|---|---|---|---|---|
| Pre-test 1 | 3800 ± 10% | 4129 | 3000 ± 10% | 2553 |
| Pre-test 2 | 3800 ± 10% | 4155 | 3000 ± 10% | 2853 |
| Pre-test 3 | 3800 ± 10% | 4104 | 3000 ± 10% | 3010 |
| Post-test 1 | 3800 ± 10% | 3973 | 3000 ± 10% | 3075 |
| Post-test 2 | 3800 ± 10% | 3920 | 3000 ± 10% | 2997 |
| Post-test 3 | 3800 ± 10% | 4091 | 3000 ± 10% | 3106 |

The total number of 10-25 um and >25 um particles released by the Catheters A, B, and C patterns per procedural step are shown in Tables 8 and 9.

TABLE 8

| Catheter Size | 10-25 um Particles Released Per Procedural Step | | | |
|---|---|---|---|---|
|  | Pre-Track | Post-Track | Post Expansion To RBP | Total |
| 2.5 × 8 mm | 189 | 283 | 621 | 1093 |
| 3.0 × 15 mm | 175 | 175 | 425 | 775 |
| 4.0 × 38 mm | 389 | 401 | 1253 | 2043 |

TABLE 9

| Size | >25 um Particles Released Per Procedural Step | | | |
|---|---|---|---|---|
|  | Pre-Track | Post-Track | Post Expansion To RBP | Total |
| 2.5 × 8 mm (A) | 21 | 32 | 58 | 110 |
| 3.0 × 15 mm (B) | 20 | 20 | 44 | 84 |
| 4.0 × 38 mm (C) | 52 | 48 | 98 | 198 |

Contribution of the competitive catheter C to the catheter particle count, as shown by the total number of 10-25 um and >25 um particles released per procedural step are shown in Tables 10 and 11. The data presented is average of 4 units. The number of 10-25 and >25 um particles generated by competitor devices, A and B, per procedural steps described above.

TABLE 10

| Device Type | 10-25 um Particles Released Per Procedural Step | | | |
|---|---|---|---|---|
|  | Pre-Track | Post-Track | Post Expansion To RBP | Total |
| Catheter 3.0 × 15 mm | 175 | 175 | 425 | 775 |
| Competitive Catheter C with 3.0 × 15 mm Balloon (no stent) | 159 | 57 | 170 | 386 |

TABLE 11

| Device Type | >25 um Particles Released Per Procedural Step | | | |
|---|---|---|---|---|
|  | Pre-Track | Post-Track | Post Expansion To RBP | Total |
| Catheter 3.0 × 15 mm | 20 | 20 | 44 | 84 |
| Competitive Catheter C with 3.0 × 15 mm Balloon (no stent) | 20 | 12 | 38 | 71 |

The following is the total number of 10-25 and >25 um particles released per by catheters A, B, and C, and 10-25 um and >25 um particles released from competitive catheters A and B, as shown in Tables 12-15.

TABLE 12

10-25 um Particles Released Per Procedural Step 1

| Device Type | Pre-Track | Post-Track | Post Expansion To RBP | Total |
|---|---|---|---|---|
| Catheter, 3.0 × 15 mm | 175 | 175 | 425 | 775 |
| Competitive Catheter A, 3.0 × 18 mm | 86 | 118 | 485 | 690 |
| Competitive Catheter B, 3.0 × 15 mm | 228 | 460 | 2454 | 3142 |

TABLE 13

>25 um Particles Released Per Procedural Step

| Device Type | Pre-Track | Post-Track | Post Expansion To RBP | Total |
|---|---|---|---|---|
| Catheter, 3.0 × 15 mm | 20 | 20 | 44 | 84 |
| Competitive Catheter A, 3.0 × 18 mm | 22 | 23 | 44 | 89 |
| Competitive Catheter B, 3.0 × 15 mm | 33 | 44 | 81 | 158 |

TABLE 14

| Total Number of Particles Generated Per Device | 2.5 × 8 mm (A) | 3.0 × 15 mm (B) | 4.0 × 38 mm (C) |
|---|---|---|---|
| 10-25 um | 1093 | 775 | 2043 |
| >25 um | 110 | 84 | 198 |

TABLE 15

| Total Number of Particles Generated Per Device | Catheter, 3.0 × 15 mm | Competitive Catheter A, 3.0 × 18 mm | Competitive Catheter B, 3.0 × 15 mm |
|---|---|---|---|
| 10-25 um | 775 | 690 | 3142 |
| >25 um | 84 | 89 | 158 |

Overall the number of standard particles recovered from the tortuous model was within ±10% of the injected number. Hence, the model was verified before and after starting each round of testing. Tables 16 to 18 lists the results of the particles measurements for each of the devices tested above. Table 16 lists catheters A, B, and C (e.g., N, J, and K patterns). Table 17 lists a test catheter and competitive catheter C (no stent). Table 18 lists test catheter and competitive catheters A and B.

TABLE 16

10-25 um And >25 um Particles Released Per Procedural Step

| | Pre-Track | | Post-Track | | Post Expansion To RBP | | Total | |
|---|---|---|---|---|---|---|---|---|
| Size | 10-25 um | >25 um | 10-25 um | >25 um | 10-25 um | >25 um | 10-25 um | >25 um |
| 2.5 × 8 mm | 189 | 21 | 283 | 32 | 621 | 58 | 1093 | 110 |
| 3.0 × 15 mm | 175 | 20 | 175 | 20 | 425 | 44 | 775 | 84 |
| 4.0 × 38 mm | 389 | 52 | 401 | 48 | 1253 | 98 | 2043 | 198 |

TABLE 17

10-25 um And >25 um Particles Released Per Procedural Step

| | Pre-Track | | Post-Track | | Post Expansion To RBP | | Total | |
|---|---|---|---|---|---|---|---|---|
| Size | 10-25 um | >25 um | 10-25 um | >25 um | 10-25 um | >25 um | 10-25 um | >25 um |
| 3.0 × 15 mm, catheter | 175 | 20 | 175 | 20 | 425 | 44 | 775 | 84 |
| 3.0 × 15 mm, Competitive Catheter C | 159 | 20 | 57 | 12 | 170 | 38 | 386 | 71 |

TABLE 18

| Device Type | Test catheter, 3.0 × 15 mm | Competitive Catheter A, 3.0 × 18 mm | Competitive Catheter B, 3.0 × 15 mm |
|---|---|---|---|
| Total Number of 10-25 um (Average of 4) | 775 | 690 | 3142 |
| Total Number of >25 um (Average of 4) | 84 | 89 | 158 |

Competitive catheter C contributed approximately 50% to the 10-25 um Applicants' device particle count and 80% to the >25 um particle count. The total number of particles generated by the test catheter was similar to that of competitive catheter A and lower than that of competitive catheter B. All sizes of the test catheters tested passed the USP 788 standard for small volume injectibles. No statistical significance was seen between the test catheters and competitor catheter C test groups for both 10-25 and >25 um particle sizes. The counts generated by competitive catheter B were statistically significant from both the test catheters and competitor catheter A for both particle sizes.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended. Accordingly, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for measuring particles generated from a medical device during a simulated clinical application, said method comprising:
   arranging an apparatus to include pretest tubing fluidly coupled with test tubing;
   introducing a medical device into the test tubing;
   positioning the medical device in a bent portion of the test tubing;
   flowing a fluid through the pretest tubing;
   flowing the fluid past the medical device;
   flowing the fluid through the test tubing; and
   counting particles in the fluid downstream from the medical device with a particle counter, wherein the counting includes measuring the particles generated by the medical device positioned in at least one of the following:
   upstream of the bent portion of the test tubing;
   within the bent portion of the test tubing; or
   downstream from bent portion of the test tubing.

2. A method for measuring particles generated from a medical device during a simulated clinical application, said method comprising:
   arranging an apparatus to include pretest tubing fluidly coupled with test tubing;
   introducing a medical device into the test tubing;
   positioning the medical device in a straight portion of the test tubing that is downstream from a bent portion of the test tubing;
   flowing a fluid through the pretest tubing;
   flowing the fluid past the medical device;
   flowing the fluid through the test tubing; and
   counting particles in the fluid downstream from the medical device with a particle counter, wherein the counting includes measuring the particles generated by the medical device positioned in at least one of the following:
   upstream of the bent portion of the test tubing;
   within the bent portion of the test tubing; or
   within the straight portion of the test tubing.

3. A method for measuring particles generated from a medical device during a simulated clinical application, said method comprising:
   arranging an apparatus to include pretest tubing fluidly coupled with test tubing;
   introducing a medical device into the test tubing;
   passing the medical device through a tortuous pathway of the test tubing;
   flowing a fluid through the pretest tubing;
   flowing the fluid past the medical device;
   flowing the fluid through the test tubing; and counting particles in the fluid downstream from the medical device with a particle counter, wherein the counting includes measuring the particles generated by the medical device positioned in at least one of the following:
   upstream of the tortuous pathway of the test tubing;
   within the tortuous pathway of the test tubing; or
   downstream from the tortuous pathway of the test tubing.

4. A method for measuring particles generated from a medical device during a simulated clinical application, said method comprising:
   arranging a platform to include pretest tubing disposed in a pretest receptacle in said platform and test tubing disposed in a test receptacle in said platform such that the test tubing includes at least one straight portion, at least one bent portion, and at least one tortuous pathway portion;
   introducing a medical device into the test tubing, where the introducing includes at least one of positioning the medical device in the bent portion of the test tubing, positioning the medical device in the straight portion of the test tubing that is downstream from the bent portion of the test tubing, or passing the medical device through the tortuous pathway of the test tubing;
   pumping a fluid through the pretest tubing with a pump;
   pumping the fluid past the medical device;
   pumping the fluid through the test tubing; and
   counting particles in the fluid downstream from the medical device with a particle counter.

5. The method as in claim 4, further comprising at least one of the following:
   monitoring the flow rate of the fluid with a flow meter;
   controlling the temperature of the fluid with a temperature controller;
   counting the particles in real time;
   counting the particles after the fluid has been collected in a container;
   re-circulating the fluid; or
   passing the fluid past the medical device in a single pass.

6. The method as in claim 5, further comprising:
   receiving data into a computing system from at least one of said temperature controller, pump, flow meter, or particle counter;

processing the data in said computing system; and transmitting instruction data from said computing system to said at least one of said temperature controller, pump, flow meter, or particle counter.

7. The method as in claim 4, further comprising at least one of the following:
introducing the medical device into a medical device receptacle in the platform;
introducing the pretest tubing into the pretest tubing receptacle; or
introducing the test tubing into the test tubing receptacle.

8. The method as in claim 4, further comprising counting particles in the fluid downstream from the test tubing before the medical device is introduced into the test tubing.

9. The method as in claim 4, further comprising:
positioning the medical device in the bent portion of the test tubing; and measuring the particles generated by the medical device positioned in at least one of the following:
upstream of the bent portion of the test tubing;
within the bent portion of the test tubing; or
downstream from bent portion of the test tubing.

10. The method as in claim 4, further comprising:
positioning the medical device in the straight portion of the test tubing that is downstream from the bent portion of the test tubing; and
measuring the particles generated by the medical device positioned in at least one of the following:
upstream of the bent portion of the test tubing;
within the bent portion of the test tubing; or
within the straight portion of the test tubing.

11. The method as in claim 4, further comprising:
passing the medical device through the tortuous pathway of the test tubing; and
measuring the particles generated by the medical device positioned in at least one of the following:
upstream of the tortuous pathway of the test tubing;
within the tortuous pathway of the test tubing; or
downstream from the tortuous pathway of the test tubing.

12. The method as in claim 4, further comprising:
introducing control particles into the fluid;
determining the amount of control particles in the counted particles; and
determining the amount of particles generated by the medical device.

13. The method as in claim 1, further comprising at least one of the following:
monitoring the flow rate of the fluid with a flow meter;
controlling the temperature of the fluid with a temperature controller;
controlling the flow rate of the fluid with a pump;
counting the particles in real time;
counting the particles after the fluid has been collected in a container;
re-circulating the fluid; or
passing the fluid past the medical device in a single pass.

14. The method as in claim 1, further comprising:
receiving data into a computing system from at least one of said temperature controller, pump, flow meter, or particle counter; processing the data in said computing system; and transmitting instruction data from said computing system to said at least one of said temperature controller, pump, flow meter, or particle counter.

15. The method as in claim 1, further comprising counting particles in the fluid downstream from the test tubing before the medical device is introduced into the test tubing.

16. The method as in claim 2, further comprising at least one of the following:
monitoring the flow rate of the fluid with a flow meter;
controlling the temperature of the fluid with a temperature controller;
controlling the flow rate of the fluid with a pump;
counting the particles in real time; counting the particles after the fluid has been collected in a container; re-circulating the fluid;
passing the fluid past the medical device in a single pass; or
counting particles in the fluid downstream from the test tubing before the medical device is introduced into the test tubing.

17. The method as in claim 2, further comprising:
receiving data into a computing system from at least one of said temperature controller, pump, flow meter, or particle counter;
processing the data in said computing system; and
transmitting instruction data from said computing system to said at least one of said temperature controller, pump, flow meter, or particle counter.

18. The method as in claim 3, further comprising at least one of the following:
monitoring the flow rate of the fluid with a flow meter;
controlling the temperature of the fluid with a temperature controller;
controlling the flow rate of the fluid with a pump;
counting the particles in real time;
counting the particles after the fluid has been collected in a container;
re-circulating the fluid; passing the fluid past the medical device in a single pass; or
counting particles in the fluid downstream from the test tubing before the medical device is introduced into the test tubing.

19. The method as in claim 3, further comprising:
receiving data into a computing system from at least one of said temperature controller, pump, flow meter, or particle counter;
processing the data in said computing system; and
transmitting instruction data from said computing system to said at least one of said temperature controller, pump, flow meter, or particle counter.

* * * * *